(12) United States Patent
Typpo et al.

(10) Patent No.: US 6,498,646 B1
(45) Date of Patent: Dec. 24, 2002

(54) APPARATUS AND PROCESS FOR DETERMINING THE PROPERTIES OF A MATERIAL WEB

(75) Inventors: Pekka M. Typpo, Cupertino, CA (US); Wolfgang Griech, Heidenheim (DE)

(73) Assignee: Voith Sulzer Papiertechnik Patent GmbH, Heidenheim (DE)

( * ) Notice: Subject to any disclaimer, the term of this patent is extended or adjusted under 35 U.S.C. 154(b) by 0 days.

(21) Appl. No.: 09/534,330

(22) Filed: Mar. 24, 2000

(30) Foreign Application Priority Data

Mar. 26, 1999 (DE) .......................... 199 13 929

(51) Int. Cl.$^7$ ............................................. G01N 21/84
(52) U.S. Cl. ...................................................... 356/429
(58) Field of Search ................................... 356/429, 430, 356/431, 237.1, 237.6, 238.1, 238.3, 239.1, 239.8

(56) References Cited

U.S. PATENT DOCUMENTS

| | | | | |
|---|---|---|---|---|
| 3,859,538 A | * | 1/1975 | Mannonen | 250/572 |
| 4,747,117 A | * | 5/1988 | Albrecht et al. | 378/19 |
| 5,010,766 A | | 4/1991 | Typpo | |
| 5,162,660 A | * | 11/1992 | Popil | 250/561 |
| 5,233,195 A | | 8/1993 | Hellstrom et al. | |
| 5,395,027 A | * | 3/1995 | Erhardt | 226/24 |
| 5,590,169 A | | 12/1996 | Monteiro | |
| 5,991,046 A | * | 11/1999 | Shakespeare et al. | 356/429 |

FOREIGN PATENT DOCUMENTS

| | | |
|---|---|---|
| DE | 1812893 | 6/1970 |
| DE | 3423308 | 1/1986 |
| DE | 3607593 | 9/1986 |
| DE | 3707107 | 9/1988 |
| DE | 19524858 | 1/1997 |
| DE | 19545340 | 6/1997 |
| DE | 19722482 | 12/1998 |
| EP | 0628808 | 12/1994 |
| WO | 94/29700 | 12/1994 |
| WO | 97/21027 | 6/1997 |

OTHER PUBLICATIONS

Chen et al., *Control System '98*, Information Tools to Match the Evolving Operator Role, Sep. 1–3, 1998, Porvoo, Finland.
Seitz, "Optische Sensoren mit eingebautem Masstab", Techinsche Rundschau, 44/90, pp. 38–47.
Patent Abstracts of Japan, JP 60–23008 A, pp. 446, Apr. 15, 1986, vol. 10, No. 9.

* cited by examiner

*Primary Examiner*—Frank G. Font
*Assistant Examiner*—Tu T. Nguyen
(74) *Attorney, Agent, or Firm*—Greenblum & Bernstein, P.L.C.

(57) ABSTRACT

Apparatus and process for determining the properties of a material web. The apparatus includes at least one radiation source, and at least one detection device adapted to detect radiation emitted from the at least one radiation source that at least one of penetrates and is reflected by the material web. The detection device can include at least one detection area unevenly divided into a plurality of individual sensors. Further, the material web can be a paper web. The invention relates to a device and a process for determining the properties of a material web, particularly a paper web, having at least one radiation source and at least one detection device for radiation that is emitted by the radiation source and that penetrates and/or is reflected by the material web, said detection device having at least one detection area unevenly divided into a large number of individual sensors.

54 Claims, 1 Drawing Sheet

APPARATUS AND PROCESS FOR DETERMINING THE PROPERTIES OF A MATERIAL WEB

CROSS-REFERENCE TO RELATED APPLICATIONS

The present application claims priority under 35 U.S.C. § 119 of German Patent Application No. 199 13 929.6, filed on Mar. 26, 1999, the disclosure of which is expressly incorporated by reference herein in its entirety.

BACKGROUND OF THE INVENTION

1. Field of the Invention

The present invention relates to a device for determining the properties of a material web, e.g., a paper web, having at least one radiation source and at least one identification device for radiation that is emitted by the radiation source and that penetrates the material web and/or is reflected by the material web.

2. Discussion of Background Information

Devices of the type generally disclosed above are known, e.g., from U.S. Pat. No. 5,233,195, which describes the use of a β-emitter and an X ray source, as well as an ionization chamber as a detection device. Known from U.S. Pat. No. 5,010,766 is a plate divided into four sections, which is provided on one side of a moving web that is being examined. The plate interacts with a configuration of four eddy current sensors on the other side of the web. In the article (ISBN 952-5183-09-2) "Paper Machine Applications with Fullsheet Imaging Measurement" by Shih-Chin Chen et al., pages 330–337, Control Systems '98, "Information Tools to Match the Evolving Operator Role," Sep. 1–3, 1998, Porvoo, Finland, a configuration comprising a light source, CCD cameras, and high speed processors is mentioned, where the light from the light source transmitted by a moving web is detected by CCD cameras.

SUMMARY OF THE INVENTION

The present invention provides an apparatus and a process which permit examination of a material web with a high degree of accuracy, particularly with respect to a number of different properties of the material web.

According to an exemplary embodiment of the invention, the detection device includes at least one detection area that is divided in non-uniform fashion into a large number of individual sensors.

The division of the detection area of the detection device permits examination of the material web that is both locally and temporally differentiated, because part of the radiation that strikes one of the individual sensors is characteristic of an area of the material web that was either penetrated or reflected by the given radiation. With a rapid read-out of the individual sensors belonging to the detection device, momentary pictures of the material web with respect to the properties under examination can be prepared in rapid sequence which, in principle, permits a seamless examination of the material web. The local resolution achievable with the invention is limited only by the size of the individual sensors. In principle, therefore, any desired level can be selected.

The non-uniform division of the detection area provided by the invention allows for an advantageous adjustment of the detection device to the conditions characteristic of the given measurement. In a particular embodiment, the movement of the material web relative to the detection device can be taken into account by the length of the individual detection areas of at least several of the individual sensors in the travel direction of the material web exceeding the length extending in the direction cross-wise thereto. In general, the individual sensors forming the detection area can differ with respect to the size and/or the shape of their individual detection areas.

According to another exemplary embodiment of the invention, it is also possible to vary the number of individual sensors per surface unit over the detection area. For example, it can be arranged in such a way that the number of individual sensors per surface unit in a central zone of the detection area is greater than in at least one marginal zone of the detection area. An optimal relation can be achieved thereby between the signal/noise ratio and the total number of sensors.

In another particular embodiment of the invention, the individual sensors can be microprocessors which, e.g., have individual detection areas of less than approximately 1 cm$^2$, preferably of about 1 mm$^2$.

In another embodiment of the invention, a 10×10 (or 100 total) array of microsensors, each with a square detection area of approximately 1 mm$^2$, can be positioned in checkerboard pattern. In this manner, the microsensors can form a continuous, square detection zone that may be positioned in a center of a detection area. The detection area can also include marginal zones formed, e.g., of oblong, particularly rectangular, microsensors having individual detection areas of several mm$^2$ and having longitudinal axes oriented in the web travel direction.

It is noted that it is fundamentally possible to utilize any desired geometric arrangement of the individual sensors. For example, the detection areas, at least in certain zones, can be provided in the form of concentrically positioned, ring-shaped individual sensors. Further, the given detection zone, or the entire detection area, can be, e.g., rectangular, circular, or triangular.

Furthermore, the detection area according to the invention can include a plurality of detection zones formed of individual sensors which are, e.g., staggered or offset relative to one another or which can be movably positioned.

In another embodiment of the invention, the microsensors can be semiconductor detectors, e.g., semiconductor sensors of very pure silicon manufactured especially for detecting electromagnetic radiation or electrically charged particles. In principle, it is also possible to use other radiation detectors, e.g., ionization detectors (such as ionization chambers) or scintillation detectors (such as scintillation tubes).

In principle, the device according to the invention can be provided with an approximately point-like radiation source that emits radiation in a specific solid-angular area. The radiation emitted by a point radiation source can also be widened by additional devices to permit planar radiation of the material web. It may be preferable for the radiation source to be designed in such a way that a radiation surface is provided. Further, the shape of the radiation area of the radiation source may preferably correspond to that of the detection area of the detection device.

It is also possible to provide a plurality of individual radiation sources instead of a single radiation source and to arrange those sources in the form of a source array.

It may be preferable for the radiation source, in keeping with the above-noted features of the invention, to be designed to provide a substantially homogeneous or uniform distribution of radiation intensity when no material is located in the radiation path.

The radiation source can be designed to release radiation with a constant intensity over time or with an intensity that is preferably varied in regular fashion, specifically a pulsing intensity. The radiation used can be of an electromagnetic type, particularly that provided by microwaves, LED light, laser beams, or X rays. In cases in which pulsed radiation is used, LEDs or lasers are the preferred radiation source. The given radiation source can be designed so as to permit adjustment of the wavelength of the electromagnetic radiation. It is also possible to use radiation sources with different wavelengths simultaneously. In principle, it is also possible to combine sources using different types of radiation.

In another possible embodiment of the invention, the radiation source is designed to radiate electrically charged particles and is particularly designed as an α-emitter and/or a β-emitter.

During operation of the device according to the invention, it may be preferable to position the radiation source on one side of the material web and the detection device on the other side, so that radiation penetrating the material web will be recorded. In principle, it is also possible to position the radiation source and the detection device on the same side of the material web and to detect the radiation reflected from the material web. Moreover, transmission and reflection measurements can be combined such that both radiation penetrating the material web and radiation reflected by the material web are detected, e.g., in conjunction with axial sensors.

Especially in conjunction with electromagnetic radiation, it is possible for at least one component assigned to the radiation source or the detection device to be positioned in the diffusion path of the radiation source, such that the component will modify at least one property of the radiation. This kind of component might be, e.g., a diffraction grid, which is positioned either close to the detection device or close to the radiation source. The spectral analysis of emitted radiation from this kind of grid can be used in a traversing measurement in which the device according to the invention is moved cross-wise to the material web travel direction to examine the properties of the material web which are dependent on the wavelength of the radiation interacting with the material web. It is also possible to install, e.g., a polarization filter in the radiation path of the device, according to the invention.

The radiation source and/or the detection device can, e.g., be positioned substantially cross-wise to the material web travel direction in swiveling or movable fashion, in order to execute any desired relative motion between the device according to the invention and a moving material web.

The present invention is also directed to a process in which at least one device of the type described above is utilized to determine the properties of a material web, e.g., a paper web.

In a particular embodiment of the process, the signals delivered by the individual sensors can be evaluated independently of one another. Thus, each individual sensor can deliver a measurement for a specific area of the material web. In this manner, comparatively large-scale momentary pictures of the material web can be compiled which permit precise examination of a local distribution of a property or properties of the material web to be performed.

According to another embodiment of the invention, the signals of at least one group of individual sensors, preferably forming a continuous detection zone in the detection area, may be compiled and, in particular, can be employed to form a mean value.

It is possible to considerably enhance the accuracy of the measured values which can be obtained with this kind of compilation by providing a large number of individual sensors per detection area. As an alternative to the formation of a mean value, or in addition thereto, the signal-to-noise ratio can be improved, and the measuring accuracy thus increased, by applying complex filtering algorithms (e.g., locally distributed Kalman filters). In this regard, the improvement is proportional, at least in theory, to $1/\sqrt{n}$, where n is the number of the individual sensors included in the given instance of signal processing.

According to another exemplary embodiment of the process according to the invention, it is possible to swivel or move the radiation source and/or the detection device as a function of the speed of the moving material web.

In this regard, it is possible to achieve a maximum degree of local and temporal resolution, or measuring accuracy, with a minimum number of individual sensors, particularly when the detection area is subdivided according to the web speed and the swiveling or traversing speed, as well as the size, form, and orientation of the individual sensors.

A particular application of the device or process according to the invention includes determining the basis weight of the material web. Due to the good temporal and spatial resolution that can be achieved with the invention by providing a large number of individual sensors that form an unevenly distributed detection area, the invention makes it simultaneously possible to determine the microformation of the material web when the individual sensors are appropriately small.

The invention also makes it possible to identify the border of the material web and thus to determine the exact location of the lateral edges of the material web.

The present invention is directed to an apparatus for determining the properties of a material web that includes at least one radiation source, and at least one detection device adapted to detect radiation emitted from the at least one radiation source that at least one of penetrates and is reflected by the material web. The detection device can include at least one detection area unevenly divided into a plurality of individual sensors. Further, the material web can be a paper web.

According to a feature of the instant invention, individual detection areas of the plurality of individual sensors can differ with respect to at least one of size and form.

In accordance with another feature of the invention, a number of the plurality of individual sensors per surface unit may vary over the at least one detection area. Further, the number of individual sensors per surface unit may be larger in a central zone of the detection area than in at least one rim zone of the detection area.

According to an aspect of the present invention, the detection area can include a plurality of detection zones formed in differing fashion by the plurality of individual sensors. The detection zones may be arranged in one of an offset and staggered fashion relative to one another.

In accordance with another aspect of the instant invention, the detection area can include at least two detection zones in which structurally equivalent ones of the plurality of individual sensors are combined. The structurally equivalent ones of the plurality of individual sensors can have at least one of common sizes and forms of individual detection areas of the individual sensors.

In accordance with a further feature of the invention, individual detection areas of at least some of the plurality of individual sensors may be oblong in form. The oblong form can be one of rectangular and trapezoidal.

According to still another feature of the invention, individual detection areas of at least several of the plurality of individual sensors may extend further in a web travel direction than in a direction cross-wise to the web travel direction.

Further, the detection area can include a plurality of zones, and the detection area, in at least one of the plurality of zones, may be arranged as a single-row of individual sensors.

At least several of the plurality of individual sensors can include microsensors. The microsensors can have an individual detection area of less than approximately 1 $cm^2$. Further, the microsensors can have individual detection area of less than several $mm^2$. The microsensors can also have an individual detection area of less than approximately 1 $mm^2$.

In accordance with a further aspect of the instant invention, the detection area can include a plurality of zones, and the detection area, in at least one of the plurality of zones, can include concentrically arranged, ring-shaped individual sensors.

According to a still further feature of the invention, the detection area can be one of approximately rectangular, circular, and triangular.

According to still another feature of the present invention, the plurality of individual sensors may include semiconductor detectors.

The plurality of individual sensors may include at least one of ionization detectors and scintillation detectors. The ionization detectors can include ionization chambers and the scintillation detectors can include scintillation tubes.

Moreover, the at least one radiation source can include a radiating surface and the radiating surface can be structured to at least approximately correspond to the at least one detection area.

Further, the at least one radiation source can include a plurality of individual radiation sources arranged as a source array.

The at least one radiation source can be adapted to provide a homogeneous distribution of radiation intensity onto the at least one detection area.

Another feature of the present invention is that at least one radiation source can be adapted to release radiation with at least one of a constant intensity over time and a regularly varying intensity. The regularly varying intensity can include a pulsing intensity.

Still another feature of the instant invention is that the at least one radiation source can be adapted to radiate at least one of electromagnetic radiation, LED light, laser beams, and X rays. The electromagnetic radiation may include microwaves.

In a further feature of the present invention, the at least one radiation source can be adapted to radiate electrically charged particles. The at least one radiation source may include at least one of an α-emitter and/or a β-emitter.

A still further feature of the invention can include at least one component assigned to one of the at least one radiation source and the at least one detection device, and the at least one component being positionable in a diffusion path of the at least one radiation source. In this manner, at least one property of the radiation can be modified. The at least one component can be an optical component, and the optical component can include a diffraction grid or polarization filter.

According to another aspect of the invention, at least one of the at least one radiation source and the at least one detection device may be one of swivelable and movable. The at least one of the at least one radiation source and the at least one detection device can be one of swivelable and movable substantially cross-wise to a web travel direction.

The present invention is directed to a process for determining the properties of a material web with at least one apparatus that include at least one radiation source and at least one detection device including at least one detection area unevenly divided into a plurality of individual sensors. The process can include directing radiation from the at least one radiation source toward the material web, and detecting, on the unevenly divided plurality of individual sensors, the emitted radiation from the at least one radiation source which at least one of penetrates and is reflected by the material web.

According to a feature of the invention, the process can further include determining a profile of at least one property of the material web. The profile of the at least one property can be determined at least one of substantially in and cross-wise to a web travel direction.

In accordance with another feature of the present invention, the process may further include obtaining a two-dimensional picture of the material web with respect to at least one property of the material web to be determined.

A further feature of the invention can include modifying at least one property of the radiation by at least one component positioned in a diffusion path of the radiation.

Still another feature of the present invention can include modifying at least one property of the radiation in accordance with at least one of a direction and a speed of at least one of the at least one radiation source and the at least one detection device relative to the material web.

The process can also include reading out data from the individual sensors in one of a parallel and sequential fashion at high speed. The individual sensors can include a CCD camera.

According to still another feature of the present invention, signals delivered by the individual sensors may be evaluated independently of one another.

The signals of at least one group of the individual sensors which are arranged to form a continuous detection zone in the detection area may be compiled and utilized to form a mean value.

In accordance with a further feature of the instant invention, a basis weight of the material web may be determined.

According to a still further feature of the present invention, formation of the material web may be determined. Further, microformation of the material web can be determined.

In accordance with still another feature of the invention, the material web includes lateral edges, and a position of at least one of the lateral edges of the material web can be determined.

According to another feature of the instant invention, at least one of the at least one radiation source and the at least one detection device can be one of swivelable and movable dependent upon a speed of the moving material web.

The present invention is directed to an apparatus for determining the properties of a material web that includes at least one radiation source and at least one detection device adapted to detect radiation emitted from the at least one radiation source that at least one of penetrates and is reflected by the material web. The detection device includes at least one detection area non-uniformly divided into a plurality of individual sensors, such that some of the plurality of individual sensors are arranged to extend further in a web travel direction than in a direction cross-wise to the web travel direction.

In accordance with yet another feature of the present invention, the detection area can include a plurality of zones, and, in at least one of the plurality of zones, the some of the plurality of individual sensors arranged to extend further in the web travel direction than in the direction cross-wise to the travel direction are arranged as a single-row of individual sensors. Further, in at least another of the plurality of zones, others of the plurality of individual sensor are substantially square shaped and arranged in a checkerboard fashion.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein.

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figure 1:
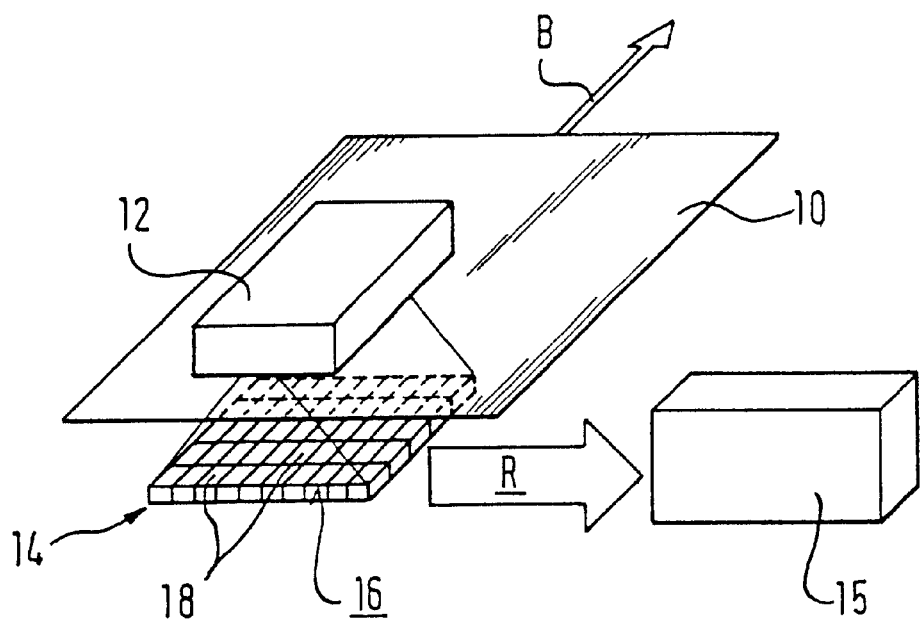
FIG. 1 illustrates a schematic depiction of an embodiment of an apparatus according to the invention.

FIG. 1 schematically illustrates a device in accordance with the features of the instant invention for determining specific properties, e.g., surface area and formation (or microformation), of a moving paper web 10. A travel direction of paper web 10 is indicated by arrow B.

The device, which includes a radiation source 12 and a detection device 14, can, in principle, be positioned in any desired section of the paper machine in which paper web 10 is manufactured. Fundamentally, the present invention can be used to examine any desired material web.

Radiation emitted by radiation source 12 can penetrate paper web 10 and can strike detection area 16 of detection device 14. Detection device 14 includes a large number of individual sensors 18 jointly forming detection area 16 which, as depicted in FIG. 1, is non-uniformly divided. In this regard, it is noted that the term "non-uniformly divided" refers to individual sensors 18 having rectangular individual detection areas which extend further in web travel direction B than in the direction cross-wise thereto. As a result, a distance from one individual sensor 18 to another individual sensor 18 situated two sensors away differs depending upon the direction, i.e., in web travel direction B, the distance between sensors is greater than in the direction cross-wise to web travel direction B. Fundamentally, this principle can be realized with other forms assumed by individual detection areas of individual sensors 18, particularly with mixed forms.

As indicated by large arrow R, the signals delivered by individual sensor 18 can be fed in the form of raw data to an evaluation unit 15, which ensures that the individual signals are correctly composed to form an image of paper web 10. In this regard, the image reproduces a local distribution of a property or properties of material web 10 being evaluated in the area penetrated or "illuminated" by the radiation. Thus, the invention can provide a high degree of temporal resolution by reading out individual sensors 18 of detection device 14 in rapid succession. Individual sensors 18 can be read out either in parallel fashion or sequentially at high speed.

Figure 2:
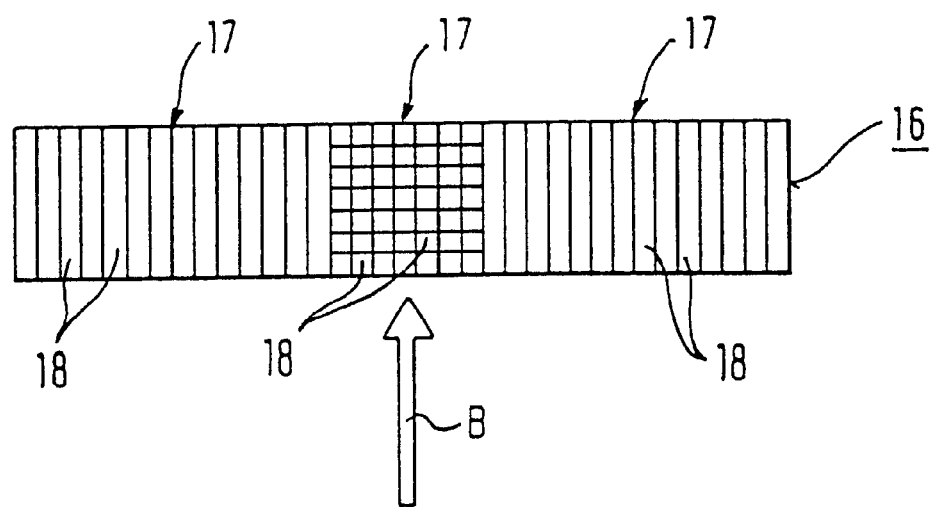
FIG. 2 illustrates an embodiment of a non-uniform subdivision of a detection area of a detection device.

FIG. 2 illustrates another example of a non-uniform division of detection area 16. In this embodiment, detection area 16 is composed of three detection zones 17, in which a central zone includes a 7×7 array of individual sensors 18 (i.e., 49 individual sensors) arranged in checkerboard pattern. In this central zone, the individual detection areas may be square in shape. However, two rim or edge areas which border on either side of the central zone include a plurality of individual sensors 18 having rectangular individual detection areas. The areas can be oriented in web travel direction B and can be provided in a single-row configuration.

While the central zone in a sense represents a two-dimensional arrangement of individual sensors 18, the arrangement of individual sensors 18 in the rim zones in a sense are positioned in a one-dimensional fashion.

Detection area 16 depicted in FIG. 2 is an example of a subdivision that is non-uniform in more than one respect, since individual detection zones 17 are different with respect to size, form, and type of configuration of individual sensors 18 (or the individual detection areas).

Furthermore, detection area 16 in FIG. 2 depicts a subdivision in which the number of individual sensors 18 per surface unit, i.e., the density of individual sensors 18, varies over detection area 16.

With respect to possible embodiments of radiation source 12 and detection device 14 according to the invention, particularly the non-uniform subdivision of detection area 16, and to the possibilities for the performance of measurements with the device according to the invention, it is noted that the radiation source can be designed to release radiation with a constant intensity over time or with an intensity that is preferably varied in regular fashion, specifically a pulsing intensity. The radiation used can be of an electromagnetic type, particularly that provided by microwaves, LED light, laser beams, or X rays. In cases in which pulsed radiation is used, LEDs or lasers may be the preferred radiation source. The given radiation source can be designed so as to permit adjustment of the wavelength of the electromagnetic radiation. It is also possible to use radiation sources with different wavelengths simultaneously. In principle, it is also possible to combine sources using different types of radiation. Moreover, radiation source 12 can be formed to radiate electrically charged particles and may be particularly formed as an α-emitter and/or a β-emitter.

As shown in the arrangement depicted in FIG. 1, it is possible to position radiation source 12 on one side of the material web and detection device 16 on the other side, so that radiation penetrating the material web will be recorded. Moreover, it is also possible to position radiation source 12 and detection device 16 on a same side of material web 10 so as to detect the radiation reflected from material web 10. Still further, it is contemplated that transmission and reflection measurements can be combined such that both radiation penetrating the material web and radiation reflected by material web 10 are detected, e.g., in conjunction with axial sensors.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

LIST OF REFERENCE CHARACTERS 10 material web, paper web
11 lateral edges
12 radiation source
14 detection device
15 evaluation unit
16 detection area
17 detection zone
18 individual sensor
B material web travel direction
R raw data

What is claimed:

1. An apparatus for determining the properties of a material web comprising:
    at least one radiation source;
    at least one detection device adapted to detect radiation emitted from said at least one radiation source that at least one of penetrates and is reflected by the material web;
    said detection device comprising at least one detection area unevenly divided into a plurality of individual sensors.

2. The apparatus according to claim 1, wherein the material web is a paper web.

3. The apparatus according to claim 1, wherein individual detection areas of said plurality of individual sensors differ with respect to at least one of size and form.

4. The apparatus according to claim 1, wherein a number of said plurality of individual sensors per surface unit varies over said at least one detection area.

5. The apparatus according to claim 4, wherein said number of individual sensors per surface unit is larger in a central zone of said detection area than in at least one rim zone of said detection area.

6. The apparatus according to claim 1, wherein said detection area comprises a plurality of detection zones formed in differing fashion by said plurality of individual sensors.

7. The apparatus according to claim 6, wherein said detection zones are arranged, in one of an offset and staggered fashion relative to one another.

8. The apparatus according to claim 1, wherein said detection area comprises at least two detection zones in which structurally equivalent ones of said plurality of individual sensors are combined.

9. The apparatus according to claim 8, wherein the structurally equivalent ones of the plurality of individual sensors have at least one of common sizes and forms of individual detection areas of said individual sensors.

10. The apparatus according to claim 1, wherein individual detection areas of at least some of said plurality of individual sensors are oblong in form.

11. The apparatus according to claim 10, wherein said oblong form is one of rectangular and trapezoidal.

12. The apparatus according to claim 1, wherein individual detection areas of at least several of said plurality of individual sensors extend further in a web travel direction than in a direction cross-wise to the web travel direction.

13. The apparatus according to claim 1, wherein said detection area comprises a plurality of zones, and
    wherein said detection area, in at least one of said plurality of zones, is arranged as a single-row of individual sensors.

14. The apparatus according to claim 1, wherein at least several of said plurality of individual sensors comprise microsensors.

15. The apparatus according to claim 14, wherein said microsensors have an individual detection area of less than approximately 1 $cm^2$.

16. The apparatus according to claim 15, wherein said microsensors have an individual detection area of less than several $mm^2$.

17. The apparatus according to claim 14, wherein said microsensors have individual detection area of less than approximately 1 $mm^2$.

18. The apparatus according to claim 1, wherein said detection area comprises a plurality of zones, and
    wherein said detection area, in at least one of said plurality of zones, comprises concentrically arranged, ring-shaped individual sensors.

19. The apparatus according to claim 1, wherein said detection area is one of approximately rectangular, circular, and triangular.

20. The apparatus according to claim 1, wherein said plurality of individual sensors comprise semiconductor detectors.

21. The apparatus according to claim 1, wherein said plurality of individual sensors comprise at least one of ionization detectors and scintillation detectors.

22. The apparatus according to claim 21, wherein said ionization detectors include ionization chambers and said scintillation detectors include scintillation tubes.

23. The apparatus according to claim 1, wherein said at least one radiation source comprises a radiating surface and said radiating surface is structured to at least approximately correspond to said at least one detection area.

24. The apparatus according to claim 1, wherein said at least one radiation source comprises a plurality of individual radiation sources arranged as a source array.

25. The apparatus according to claim 1, wherein said at least one radiation source is adapted to provide a homogeneous distribution of radiation intensity onto said at least one detection area.

26. The apparatus according to claim 1, wherein said at least one radiation source is adapted to release radiation with at least one of a constant intensity over time and a regularly varying intensity.

27. The apparatus according to claim 26, wherein said regularly varying intensity comprises a pulsing intensity.

28. The apparatus according to claim 1, wherein said at least one radiation source is adapted to radiate at least one of electromagnetic radiation, LED light, laser beams, and X rays.

29. The apparatus according to claim 28, wherein said electromagnetic radiation comprises microwaves.

30. The apparatus according to claim 1, wherein said at least one radiation source is adapted to radiate electrically charged particles.

31. The apparatus according to claim 30, wherein said at least one radiation source comprises at least one of an α-emitter and/or a β-emitter.

32. The apparatus according to claim 1, further comprising at least one component assigned to one of said at least one radiation source and said at least one detection device; and said at least one component being positionable in a diffusion path of said at least one radiation source, whereby, at least one property of the radiation is modified.

33. The apparatus according to claim 32, wherein said at least one component comprises an optical component.

34. The apparatus according to claim 33, wherein said optical component comprises a diffraction grid or polarization filter.

35. The apparatus according to claim 1, wherein at least one of said at least one radiation source and said at least one detection device are one of swivelable and movable.

36. The apparatus according to claim 35, wherein said at least one of said at least one radiation source and said at least one detection device are one of swivelable and movable substantially cross-wise to a web travel direction.

37. A process for determining the properties of a material web with at least one apparatus that includes at least one radiation source and at least one detection device including at least one detection area unevenly divided into a plurality of individual sensors, said process comprising:

directing radiation from the at least one radiation source toward the material web; and detecting, on the unevenly divided plurality of individual sensors, the emitted radiation from the at least one radiation source which at least one of penetrates and is reflected by the material web.

38. The process according to claim 37, further comprising determining a profile of at least one property of the material web.

39. The process according to claim 38, wherein the profile of the at least one property is determined at least one of substantially in and cross-wise to a web travel direction.

40. The process according to claim 37, further comprising obtaining a two-dimensional picture of the material web with respect to at least one property of the material web to be determined.

41. The process according to claim 37, further comprising modifying at least one property of the radiation by at least one component positioned in a diffusion path of the radiation.

42. The process according to claim 37, further comprising modifying at least one property of the radiation in accordance with at least one of a direction and a speed of at least one of the at least one radiation source and the at least one detection device relative to the material web.

43. The process according to claim 37, further comprising reading out data from the individual sensors in one of a parallel and sequential fashion at high speed.

44. The process according to claim 43, wherein the individual sensors comprise a CCD camera.

45. The process according to claim 37, wherein signals delivered by the individual sensors are evaluated independent of one another.

46. The process according to claim 37, wherein the signals of at least one group of the individual sensors which are arranged to form a continuous detection zone in the detection area are compiled and utilized to form a mean value.

47. The process according to claim 37, wherein a basis weight of the material web is determined.

48. The process according to claim 37, wherein formation of the material web is determined.

49. The process according to claim 48, wherein microformation of the material web is determined.

50. The process according to claim 37, wherein the material web includes lateral edges, and wherein a position of at least one of the lateral edges of the material web is determined.

51. The process according to claim 37, wherein at least one of the at least one radiation source and the at least one detection device are one of swivelable and movable dependent upon a speed of the moving material web.

52. An apparatus for determining the properties of a material web comprising:

at least one radiation source;

at least one detection device adapted to detect radiation emitted from said at least one radiation source that at least one of penetrates and is reflected by the material web;

said detection device comprising at least one detection area non-uniformly divided into a plurality of individual sensors, wherein some of said plurality of individual sensors are arranged to extend further in a web travel direction than in a direction cross-wise to the web travel direction.

53. The apparatus according to claim 52, wherein said detection area comprises a plurality of zones, and wherein, in at least one of said plurality of zones, said some of the plurality of individual sensors arranged to extend further in the web travel direction than in the direction cross-wise to the travel direction are arranged as a single-row of individual sensors.

54. The apparatus according to claim 53, wherein, in at least another of said plurality of zones, others of said plurality of individual sensor are substantially square shaped and arranged in a checkerboard fashion.

* * * * *